United States Patent [19]

El-Chahawi et al.

[11] 4,141,915

[45] Feb. 27, 1979

[54] METHOD OF PREPARING α-SUBSTITUTED CYANOACETIC ACID ALKYL ESTERS

[75] Inventors: Moustafa El-Chahawi, Troisdorf; Uwe Prange, Niederkassel; Hermann Richtzenhain, Much-Schwellenbach; Wilhelm Vogt, Cologne, all of Fed. Rep. of Germany

[73] Assignee: Dynamit Nobel Aktiengesellschaft, Troisdorf, Fed. Rep. of Germany

[21] Appl. No.: 829,177

[22] Filed: Aug. 30, 1977

[30] Foreign Application Priority Data

Sep. 1, 1976 [DE] Fed. Rep. of Germany ....... 2639327

[51] Int. Cl.² ............................................ C07C 120/00
[52] U.S. Cl. .............................. 260/465 D; 260/465.4
[58] Field of Search ......................... 260/465 D, 465.4

[56] References Cited

U.S. PATENT DOCUMENTS

| | | |
|---|---|---|
| 2,506,571 | 5/1950 | Barrick et al. ................... 260/465.6 |
| 3,116,306 | 12/1963 | Heck ................................ 260/465.4 |
| 3,210,400 | 10/1965 | Brakebill ........................... 260/465.4 |
| 3,337,603 | 8/1967 | Kato et al. ...................... 260/465.6 X |

FOREIGN PATENT DOCUMENTS

| | | |
|---|---|---|
| 42-17246 | 9/1967 | Japan ..................................... 260/465.4 |
| 45-31651 | 10/1970 | Japan ..................................... 260/465.4 |

OTHER PUBLICATIONS

Cope et al.; Org. Reactions, 9, (1957), pp. 262–271.
Abstract of Belgian Patent 828,187 of 10-21-75.
Abstract of Japanese Examined Appln. 31651/70 of 10-13-70.
Matsuda, Bull. Chem. Soc. Japan, 40 pp. 135–144 (1967).
Translation of Japanese Examined Applen. 17246/67 of 9-12-67.

*Primary Examiner*—Joseph Paul Brust
*Attorney, Agent, or Firm*—Sprung, Felfe, Horn, Lynch & Kramer

[57] ABSTRACT

A process for preparing an α-substituted cyanoacetic acid alkyl ester which comprises contacting an unsaturated nitrile of the formula

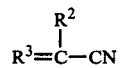

I wherein
$R^2$ is a hydrogen atom or a methyl group and
$R^3$ is $CH_2$, $CHCH_3$, $CHCN$, $CHC_6H_5$ or $C(CH_3)_2$
with an alcohol of the formula

ROH                                                                II wherein
R is a primary, secondary or tertiary saturated alkyl moiety of 1 to 20 carbon atoms and carbon monoxide in the presence of $Co_2(CO)_8$ and an α-substituted pyridine in the absence of hydrogen at an elevated temperature and pressure.

18 Claims, No Drawings

METHOD OF PREPARING α-SUBSTITUTED CYANOACETIC ACID ALKYL ESTERS

BACKGROUND OF THE INVENTION

1. Field of the Invention

The present invention relates to a method of preparing α-substituted cyanoacetic acid alkyl esters by the reaction of an α,β-olefin-unsaturated nitrile with an alkanol and carbon monoxide in the presence of $Co_2(CO)_8$ and a basically acting organic compound at elevated temperatures and pressures.

2. Discussion of the Prior Art

In a method described by Cope et al in "Org. Reactions" 9 (1957), 262–271 for the preparation of α-alkyl-substituted cyanoacetic acid esters, cyanoacetic acid ester is reacted with an alkyl halide in the presence of an alkali alcoholate and alcohol. This known method requires several expensive reaction steps and produces a considerable amount of by-products and wastes, such as inorganic salts, in addition to the desired products. This method thus becomes very uneconomical. In addition, the inorganic wastes, especially in processes performed on a commercial scale, are ballast materials which are difficult to dispose of in an ecologically sound manner.

Another known method of preparing 2-cyanopropionic acid esters (Belgian Pat. No. 828,187) consists in the reaction of cyanoacetic acid esters with formaldehyde and hydrogen in the presence of glacial acetic acid, palladium on charcoal and, for example, piperidine and hydroquinone. The yields obtained, however, are poor, ranging between 14 and 61 percent.

It is furthermore known from Japanese Examined Patent Appln. 31651/70 to react acrylonitrile with ethanol or propanol or isopropanol and carbon monoxide in the presence of $Co_2(CO)_8$. In addition to other reaction products, 2-cyanopropionic acid ethyl, n-propyl and isopropyl esters are produced, respectively, in a yield not exceeding 13 percent. The methyl ester cannot be prepared by this method.

Furthermore, a method is known from Japanese Examined Patent Appln. 17246/67 in which acrylonitrile is reacted with carbon monoxide and methanol in the presence of $Co_2(CO)_8$, pyridine and up to 10 weight percent of $H_2$, with respect to carbon monoxide, to form mixtures of 2- and 3-cyanoacetic acid methyl ester, β-cyanopropionaldehydedimethylacetal and propionitrile. The same findings are reported also in Bull. Chem. Soc., Japan, 40, 135–144 (1967).

This last-mentioned carbonylation method yields, in addition to 2-cyanopropionic acid methyl ester, considerable amounts of by-products whose separation is made difficult by close boiling points. Another disadvantage lies in the necessity of adding up to 10 weight percent of hydrogen to the carbon monoxide.

It is an object of this invention, therefore, to provide a readily available method for the preparation of α-substituted cyanoacetic acid alkyl esters whereby such α-substituted cyanoacetic acid alkyl esters can be prepared in a simple manner in a high yield from readily available materials which do not require expensive reaction steps or provide large quantities of materials which cannot be disposed of readily in an ecological manner.

SUMMARY OF THE INVENTION

Broadly, this invention contemplates a process for preparing an α-substituted cyanoacetic acid alkyl ester of the formula

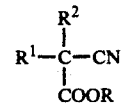

wherein

R is a primary, secondary or tertiary saturated alkyl moiety of 1 to 20 carbon atoms, $R^1$ is a methyl, ethyl, isopropyl, cyanomethyl or benzyl radical, and $R^2$ is hydrogen or methyl by a process which comprises contacting an α,β-unsaturated nitrile of the formula

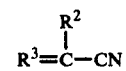

wherein $R^2$ has the meaning given above and $R^3$ is one of the moieties $CH_2$, $CHCH_3$, $CHCN$, $CHC_6H_5$ or $C(CH_3)_2$ with an alcohol of the formula

ROH        II wherein

R has the meaning given above and carbon monoxide in the absence of hydrogen and in the presence of an α-substituted pyridine and $Co_2(CO)_8$.

By the method of the invention, α-substituted cyanoacetic acid alkyl esters of the general formula

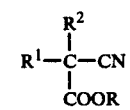

can be prepared. R and $R^2$ have the same meaning as above. The α-substituent $R^1$ is one of the moieties, methyl, ethyl, isopropyl, cyanomethyl or benzyl. Preferably, $R^2$ is a methyl group or hydrogen whenever $R^1$ is a methyl group.

Examples of products of the process are methylcyanoacetic acid alkyl ester, ethylcyanoacetic acid alkyl ester, carbalkoxysuccinic acid dinitrile, benzylcyanoacetic acid alkyl ester, dimethylcyanoacetic acid alkyl ester, and isopropylcyanoacetic acid alkyl ester.

Examples of nitriles of Formula I are acrylonitrile, methacrylonitrile, β,β-dimethylacrylonitrile, crotonic acid nitrile, fumaric acid dinitrile, and cinnamic acid nitrile. Preferred are acrylonitrile, crotonic acid nitrile, fumaric acid dinitrile and cinnamic acid nitrile.

Primary, secondary or tertiary saturated alcohols of 1 to 20 carbon atoms, preferably 1 to 4 carbon atoms, can be used as alcohols of General Formula II. Examples are methanol, ethanol, n- and iso-propanol, the butanols, the hexanols, or branched alcohols such as 2-ethylhexanol.

In general, the alcohol is used in an excess - for example in twice to six times the molar (stoichiometric) amount with respect to the α,β-unsaturated nitrile.

The carbon monoxide can be used in the pressure range from 50 to 250 bars. Higher pressures are possible, but unnecessary. Preferably the reaction is performed in the pressure range of 100 to 180 bars. The carbon monoxide can contain inert gases, such as nitrogen gas.

$Co_2(CO)_8$ is used as the catalyst, in a molar ratio of from 1:10 to 1:1000, preferably 1:50 to 1:500, with respect to the $\alpha,\beta$-unsaturated nitrile.

It is desirable to use $\alpha$-substituted pyridines whose boiling points are in a range which permits easy distillative separation from the end product. The $\alpha$-substituted pyridines that are suitable in accordance with the invention are those of the general formula:

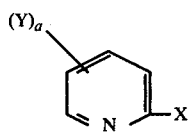

The substituent X can be a primary or secondary or tertiary alkyl moiety of 1 to 4 carbon atoms, which can be olefinically unsaturated, or a benzyl moiety which can be alkyl-substituted, or halogen, or a phenyl moiety, or an $\alpha$-pyridyl moiety.

Y can be a $C_1$ to $C_4$ alkyl moiety (primary, secondary or tertiary, saturated) or halogen. a is 0 to 2. When a is 2, the substituents Y can be identical or different. Preferably, the substituents Y (or substituent Y) are in positions 4 and/or 6 on the nucleus. Y can be the same as or different from X.

Examples are $\alpha$-picoline, 2,4-lutidine, 2,6-lutidine, 2,4,6-collidine, 2-ethylpyridine, 2-n-propyl- and 2-isopropylpyridine, 2-n-butyl- and 2-tert.-butylpyridine, 2-vinylpyridine, 2-propenylpyridine, 2-chloropyridine, 2-bromo- and 2-iodopyridine, 2-benzylpyridine, 2-phenylpyridine and $\alpha$-$\alpha'$-bipyridyl. $\alpha$-picoline, 2,4- and 2,6-lutidine, 2,4,6-collidine, 2-ethylpyridine, 2-vinylpyridine and 2-chloropyridine have proven to be substances having good selective action.

$\alpha$-alkyl-substituted pyridines, especially methyl- or ethyl-substituted pyridines, are preferred, especially $\alpha$-picoline and 2,4-lutidine.

The pyridine derivatives are used in a molar ratio to the $\alpha,\beta$-unsaturated nitrile of from 1:1 to 1:100, preferably of from 1:10 to 1:50.

The reaction temperature can be between 100° and 250° C., preferably between 120° and 220° C.

In general, the reaction is performed such that the components are placed in an autoclave and raised to the desired reaction temperature with stirring and under pressure. It is also possible, however, to feed the $\alpha,\beta$-unsaturated nitrile to the other reactants at elevated pressure and elevated temperature.

It is desirable to largely exclude air oxygen.

Surprisingly, the preparation of the desired end products can be accomplished in a high yield and with a high degree of purity if an $\alpha$-substituted pyridine is used instead of pyridine. The presence of hydrogen in this case is unnecessary. The end products can easily be separated from the reaction mixture by distillation. The alcohol separated by the distillation and the $\alpha$-substituted pyridine can be recycled.

As Comparative Examples 1 to 12 below indicate, other amines such as pyridine, quinoline, morpholine and aliphatic primary, secondary and tertiary amines are considerably less effective, evidently because the selectivity of the reaction is poorer.

The $\alpha$-substituted cyanoacetic acid alkyl esters which are obtainable by the method of the invention are valuable chemical intermediates. For example, substituted cyanoacetic acid esters can be used for the preparation of barbituric acid derivatives by a method described in U.S. Pat. No. 3,324,125. These barbituric acid derivatives are used as medicine.

In order to more fully illustrate the nature of the invention and the manner of practicing the same, the following examples are presented:

EXAMPLES

EXAMPLE 1

In a one-liter autoclave, containing 53 g (1 mole) of acrylonitrile, 5 g of $Co_2(CO)_8$, 10 g of $\alpha$-picoline and 400 ml of ethanol were placed at room temperature. After the autoclave had been purged several times with nitrogen, a carbon monoxide cold pressure of 140 bars was established. Then the mixture was heated, with stirring, at 125° C., and held at this temperature for 2 hours. After the reaction mixture had cooled and the remaining carbon monoxide had been removed, the mixture was worked up by distillation. 121 g of methylcyanoacetic acid ethyl ester was isolated, in a purity of 99.6%. The yield was 95%, 3 g remaining in the distillation residue.

EXAMPLE 2

Under the reaction conditions described in Example 1, but with the use of 2.5 g of $Co_2(CO)_8$ and 5 g of $\alpha$-picoline, 119 g of methylcyanoacetic acid ethyl ester was obtained after working up (yield 93.8%).

EXAMPLE 3

Under the reaction conditions given in Example 1, but reducing the $Co_2(CO)_8$ to 1.5 g and using 2.5 g of $\alpha$-picoline, 115 g of methylcyanoacetic acid ethyl ester was obtained after the distillation (yield 90%). A distillation residue of 7.5 g remained.

EXAMPLE 4

In the manner described in Example 1, but using 5 g of 2,4-lutidine instead of $\alpha$-picoline, 117 g of methylcyanoacetic acid ethyl ester was obtained after the distillation (yield 92%), a distillation residue of 6 g remaining.

EXAMPLE 5

In the manner described in Example 1, but using 5 g of 2,4,6-collidine instead of $\alpha$-picoline, 110.5 g of methylcyanoacetic acid ethyl ester (yield 87%) was obtained after distillation. 8 g was undistillable.

EXAMPLE 6

Under the reaction conditions described in Example 1, but using 5 g of 2,6-lutidine instead of $\alpha$-picoline, 108 g of methylcyanoacetic acid ethyl ester was obtained by distillation after the reaction (yield 85%), 14 g of undistillable residue having been formed.

EXAMPLES 7 to 10

In Examples 7 to 10, the values listed in Table 1 were obtained using alcohols other than ethanol.

Table 1

| Ex. No. | Alcohol | Acrylonitrile | $Co_2(CO)_8$ | $\alpha$-picoline | Pressure at 20° C. | Temp. | Duration | Yield of $\alpha$-methylcyanoacetic ester |
|---|---|---|---|---|---|---|---|---|
| 7 | 500 ml | 2 moles | 10 g | 10 g | 110 | 150 | 2 | Methylcyanoacetic acid |

Table 1-continued

| Ex. No. | Alcohol | Acrylo-nitrile | Co₂(CO)₈ | α-picoline | Pressure at 20° C. | Temp. | Duration | Yield of α-methylcyano-acetic ester | |
|---|---|---|---|---|---|---|---|---|---|
| 8 | CH₃OH 500 ml isopropanol | 2 moles | 10 g | 10 g | 100 | 150 | 2 | methyl ester<br>Methylcyanoacetic acid isopropyl ester | 75%<br>93% |
| 9 | 500 ml tert.-butanol | 2 moles | 10 g | 10 g | 120 | 130–140 | 3 | Methylcyanoacetic acid tert.-butyl ester | 90% |
| 10 | 500 ml 2-ethyl-hexanol | 2 moles | 10 g | 10 g | 120 | 140 | 2 | Methylcyanoacetic acid 2-ethylhexyl ester | 85% |

EXAMPLES 11–13

In Examples 13 to 15, the reaction procedure is similar to that of Example 1, but the following α,β-unsaturated nitriles were used instead of acrylonitrile, with the results listed in Table 2.

Table 2

In each test, one mole of α,β-unsaturated nitrile, 5 g of Co₂(CO)₈, 5 g of α-picoline and 300 ml of ethanol were placed in the reactor at a CO cold pressure of 110 to 130 bars, and heated to 150° C.

| Example | α,β-unsaturated nitrile | Product and Yield |
|---|---|---|
| 11 | Crotonic acid nitrile | Ethylcyanoacetic acid ethyl ester, 95% |
| 12 | Fumaric acid dinitrile | Carbethoxysuccinic acid, dinitrile, 75% |
| 13 | Cinnamic acid nitrile | Benzylcyanoacetic acid ethyl ester, 60%<br>Phenylpropionitrile, 30% |

EXAMPLE 14

By a procedure similar to Example 1, but with methacrylonitrile as the α,β-unsaturated nitrile, it was possible to obtain dimethylcyanoacetic acid ethyl ester after distillation.

EXAMPLE 15

If, instead of acrylonitrile, as described in Example 1, β,β-dimethylacrylonitrile is used, isopropylcyanoacetic acid ethyl ester is obtained at a reaction temperature of 200° C.

COMPARATIVE EXAMPLES 1 to 12

In Comparative Examples 1 to 12, the procedure was the same as in Example 1, but other amines were used instead of α-substituted pyridines, and the results listed in Table 3 were obtained.

Table 3

In these tests, 1 mole of acrylonitrile, 400 ml of ethanol and 5 g of Co₂(CO)₈ were reacted with 10 g of amine at a CO cold pressure of 140 bars, at 125° C. for 2 to 5 hours.

| Comp. Ex. | Amine | Distillate in g | Product distribution as % of area per GC analysis | |
|---|---|---|---|---|
| 1 | triethyl-amine | 89 g | methylcyanoacetic acid ethyl ester | 40% |
| | | | 2,4-dicyan-2-methylbutyric acid ethyl ester | 51% |
| 2 | di-n-butylamine | 63 g | methylcyanoacetic acid ethyl ester | 39.2% |
| | | | β-cyanopropionic acid ethyl ester | 3.2% |
| | | | 2,4-dicyan-2-methylbutyric acid ethyl ester | 42.6% |
| 3 | di-n-propylamine | 96 g | methylcyanoacetic acid ethyl ester | 94.5 |
| | | | β-cyanopropionic acid ethyl ester | 0.3% |
| | | | 2,4-dicyan-2-methylbutyric acid ethyl ester | 0.7% |
| 4 | benzyl-amine | 45 g | methylcyanoacetic acid ethyl ester | 87.9% |
| | | | β-cyanopropionic acid ethyl ester | 2.2% |
| | | | 2,4-dicyan-2-methylbutyric acid ethyl ester | 1.8% |
| 5 | dicyclo-hexylamine | 71 g | methylcyanoacetic acid ethyl ester | 72% |
| | | | β-cyanopropionic acid ethyl ester | 1% |
| | | | 2,4-dicyan-2-methylbutyric acid ethyl ester | 17% |
| 6 | morpholine | 66 g | methylcyanoacetic acid ethyl ester | 56.3% |
| | | | β-cyanopropionic acid ethyl ester | 2% |
| | | | 2,4-dicyan-2-methylbutyric acid ethyl ester | 14.5% |
| 7 | aniline | 58 g | methylcyanoacetic acid ethyl ester | 59.5% |
| | | | β-cyanopropionic acid ethyl ester | 1.6% |
| | | | 2,4-dicyan-2-methylbutyric acid ethyl ester | 16.6% |
| 8 | pyridine | 70 g | methylcyanoacetic acid ethyl ester | 29% |
| | | | β-cyanopropionic acid | |

Table 3-continued

In these tests, 1 mole of acrylonitrile, 400 ml of ethanol and 5 g of $Co_2(CO)_8$ were reacted with 10 g of amine at a CO cold pressure of 140 bars, at 125° C for 2 to 5 hours.

| Comp. Ex. | Amine | Distillate in g | Product distribution as % of area per GC analysis | |
|---|---|---|---|---|
| | | | ethyl ester | 27.3% |
| | | | 2,4-dicyan-2-methylbutyric acid ethyl ester | 31.6% |
| 9 | quinoline | 74 g | methylcyanoacetic acid ethyl ester | 75% |
| | | | β-cyanopropionic acid ethyl ester | 0.8% |
| | | | 2,4-dicyan-2-methylbutyric acid ethyl ester | 1.6% |
| | | | β-cyanopropionaldehyde-diethylacetal | 16.6% |
| 10 | β-picoline | 62 g | methylcyanoacetic acid ethyl ester | 28.2% |
| | | | β-cyanopropionic acid ethyl ester | 29.5% |
| | | | 2,4-dicyan-2-methylbutyric acid ethyl ester | 20.5% |
| 11 | γ-picoline | 61 g | methylcyanoacetic acid ethyl ester | 33.5% |
| | | | β-cyanopropionic acid ethyl ester | 26.5% |
| | | | 2,4-dicyan-2-methylbutyric acid ethyl ester | 18.2% |
| 12 | 3,5-lutidine | | methylcyanoacetic acid ethyl ester | 50% |
| | | | β-cyanopropionic acid ethyl ester | 26.2% |
| | | | 2,4-dicyan-2-methylbutyric acid ethyl ester | 9.8% |

What is claimed is:

1. A process for preparing an α-substituted cyanoacetic acid alkyl ester of the formula

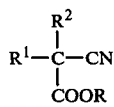   III wherein

R is a primary, secondary or tertiary saturated alkyl moiety of 1 to 20 carbon atoms, $R^1$ is methyl, ethyl, isopropyl, cyanomethyl or benzyl, $R^2$ is hydrogen or methyl which comprises contacting an α,β-unsaturated nitrile of the formula

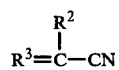   I wherein $R^2$ has the previously assigned significance and $R^3$ is $CH_2$, $CHCH_3$, $CHCN$, $CHC_6H_5$ or $C(CH_3)_2$ with an alcohol of the formula

ROH   II wherein

R has the previously assigned significance and carbon monoxide in the presence of $Co_2(CO)_8$ and an α-substituted pyridine which has the formula

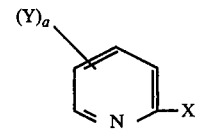

wherein

X is a primary or secondary or tertiary alkyl moiety of 1 to 4 carbon atoms, which can be olefinically unsaturated, or a benzyl moiety which can be alkyl-substituted, or halogen or a phenyl moiety, or an alpha-pyridyl moiety, Y is a $C_1$ to $C_4$ alkyl moiety or halogen, a is 0 to 2 in the absence of hydrogen at an elevated temperature and pressure.

2. A process according to claim 1 wherein the reaction is conducted at a temperature between 100° and 250° C. under an elevated pressure up to 250 bars.

3. A process according to claim 2 wherein the process is conducted under carbon monoxide pressure of 50 to 250 bars.

4. A process according to claim 3 wherein the process is conducted at a carbon monoxide pressure of 100 to 180 bars.

5. A process according to claim 3 wherein the process is conducted at a temperature between 120° and 220° C.

6. A process according to claim 2 wherein R is a primary, secondary, or tertiary saturated alkyl moiety of 1 to 4 carbon atoms.

7. A process according to claim 2 wherein said α-substituted pyridine is α-picoline, 2,4-lutidine, 2,6-lutidine, 2,4,6-collidine, 2-ethylpyridine, 2-vinylpyridine or 2-chloropyridine.

8. A process according to claim 2 wherein the molar ratio of α-substituted pyridine to nitrile is 1:1 to 1:100.

9. A process according to claim 8 wherein the molar ratio of α-substituted pyridine to nitrile is 1:10 to 1:50.

10. A process according to claim 2 wherein the α-substituted pyridine has the formula

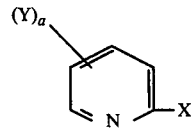

wherein
 a is 0 to 2,
 X is a primary, secondary or tertiary alkyl moiety of 1 to 4 carbon atoms which can be olefinically unsaturated or a benzyl moiety which can be alkyl-substituted or halogen or a phenyl moiety or an α-pyridyl moiety, and
 Y is a primary, secondary or tertiary saturated $C_1$-$C_4$ alkyl moiety or halogen.

11. A process according to claim 10 wherein the Y substituents are in the 4- and/or 6-position on the pyridine nucleus.

12. A process according to claim 10 wherein the α-substituted pyridine is α-picoline, 2,4-lutidine, 2,6-lutidine, 2,4,6-collidine, 2-ethylpyridine, 2-n-propyl- and 2-isopropylpyridine, 2-n-butyl- and 2-tert.-butylpyridine, 2-vinylpyridine, 2-propenylpyridine, 2-chloropyridine, 2-bromo- or 2-iodopyridine, 2-benzylpyridine, 2-phenylpyridine and α,α'-bipyridyl.

13. A process according to claim 2 wherein the $Co_2(CO)_8$ is employed in a molar amount with respect to said nitrile such that the ratio of $Co_2(CO)_8$ to nitrile is 1:10 to 1:1000.

14. A process according to claim 13 wherein the molar ratio of $Co_2(CO)_8$ to nitrile is 1:50 to 1:500.

15. A process according to claim 2 wherein the process is carried out in a closed vessel at autogeneous pressure.

16. A process according to claim 2 wherein said alcohol is ethanol, methanol, isopropanol, tertiary butanol, or 2-ethylhexanol.

17. A process according to claim 1 wherein said alpha-substituted pyridine is alpha-picoline, 2,4-lutidine, 2,6-lutidine, 2,4,6-collidine, 2-ethylpyridine, 2-n-propyl- and 2-isopropylpyridine, 2-n-butyl- and 2-tert.-butylpyridine, 2-vinylpyridine, 2-propenylpyridine, 2-chloropyridine, 2-bromo- and 2-iodopyridine, 2-benzylpyridine, 2-phenylpyridine or alpha-alpha'-bipyridyl.

18. A process according to claim 1 wherein said alpha-substituted pyridine is alpha-picoline, 2,4-lutidine, 2,6-lutidine, 2,4,6-collidine, 2-ethylpyridine, 2-n-propyl- and 2-isopropylpyridine, 2-n-butyl- and 2-tert.-butylpyridine, 2-vinylpyridine, 2-propenylpyridine, 2-chloropyridine, 2-bromo- and 2-iodopyridine, 2-benzylpyridine, 2-phenylpyridine or alpha-alpha'-bipyridyl.

* * * * *

UNITED STATES PATENT AND TRADEMARK OFFICE
CERTIFICATE OF CORRECTION

PATENT NO. : 4,141,915
DATED : February 27, 1979
INVENTOR(S) : EL-CHAHAWI et al.

It is certified that error appears in the above-identified patent and that said Letters Patent are hereby corrected as shown below:

[56] Title page, References cited headed, Other references, "Applen." should read -- Appln. --.

Claim 1, column 7, line 60, "(CO)8" should read -- $(CO)_8$ --.

Signed and Sealed this

Seventh Day of August 1979

[SEAL]

Attest:

Attesting Officer

LUTRELLE F. PARKER
Acting Commissioner of Patents and Trademarks